United States Patent [19]

Marciel

[11] Patent Number: Plant 7,613

[45] Date of Patent: Aug. 6, 1991

[54] ROSE PLANT NAMED DEVLASS

[75] Inventor: Stanley G. Marciel, Aptos, Calif.

[73] Assignee: DeVor Nurseries, Inc., Watsonville, Calif.

[21] Appl. No.: 447,656

[22] Filed: Dec. 8, 1989

[51] Int. Cl.[5] ..... A01H 5/00

[52] U.S. Cl. ..... Plt./14

[58] Field of Search ..... Plt./14, 23

*Primary Examiner*—Howard J. Locker

*Attorney, Agent, or Firm*—Charles W. Rummler

[57] ABSTRACT

A new and distinct greenhouse rose plant of the tea rose type particularly distinguished by its continuous and profuse production of relatively large high-centered flowers of pure white color from early Spring to Winter under greenhouse culture the flowers being borne singly on strong upright stems of substantial length on a vigorous upright plant having abundant foliage.

2 Drawing Sheets

BACKGROUND OF THE NEW PLANT

This new variety of rose plant originated as a seedling of a hybrid which resulted from my crossing of an unnamed and unpatented seedling with the variety Angel (U.S. Plant Pat. No. 5,172) as the pollen parent with the object of producing a long stemmed white hybrid tea rose. This crossing was done at Pleasanton, Calif. and the present seedling was selected from plants resulting from the planting of the seeds of the said hybrid in greenhouse at Pleasanton and the present seedling was selected by me for propagation because of its profuse production of pure white flowers of very fine form. Propagation was done at Pleasanton by means of budding with such satisfactory results that propagation was continued in the same manner through several successive generations which thereby demonstrated conclusively that the homogeneity of this plant could be assured.

DESCRIPTION OF THE DRAWING

My new rose plant is illustrated by the accompanying photographic drawings which show a three-quarter view of a half opened bloom, three-fourths of a face view of a mature bloom, and a bud, the sepals of which are just beginning to open, the colors shown being as nearly true to that herein specified as is reasonably possible to obtain by conventional photographic procedures.

DESCRIPTION OF THE NEW VARIETY

Figure 1:
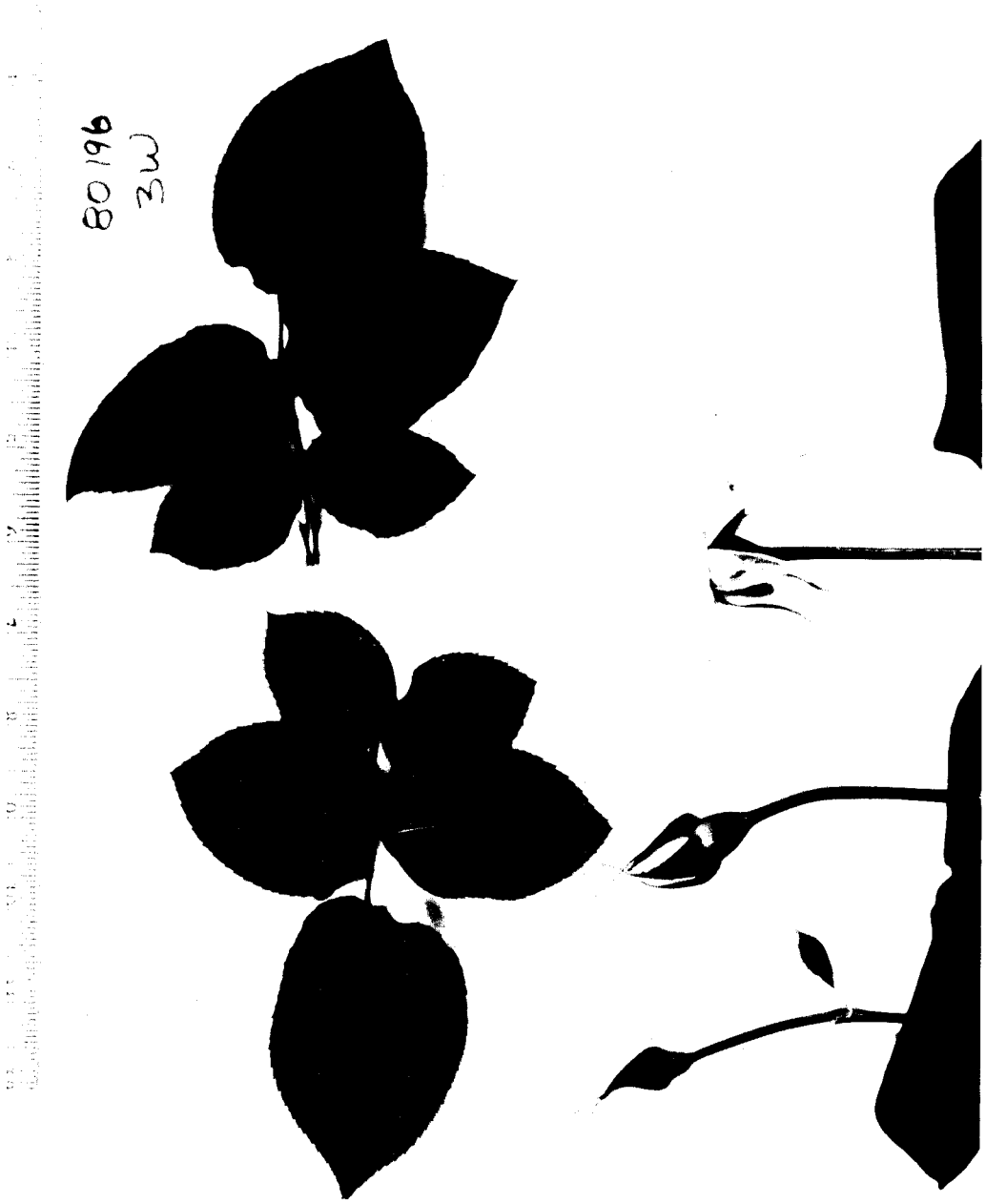

The following is a detailed description of my new greenhouse rose plant based upon observation of plants grown in greenhouse at Watsonville, Calif., the color designations being according to The R.H.S. Colour Chart published by The Royal Horticultural Society of London, England.

THE PLANT

Origin: Seedling.

Parentage:

*Seed parent.*—An unnamed and unpatented seedling.

*Pollen parent.*—The variety Angel (U.S. Plant Pat. No. 5,172).

Classification:

*Botanic.*—Hybrid Rose.

*Commercial.*—Greenhouse Rose.

Form: Upright bush.

Growth: Vigorous and very sturdy.

Branching character: Free branching.

Height: About 70 to 75 cm.

Cane length: About 64 cm.

Foliage:

*Quantity.*—Abundant.

*Number of leaves.*—About 7 or 8 before the last flower cut.

*Shape of leaf.*—Odd pinnate.

*Size.*—131 mm. long and about 9.6 cm. wide.

*Leaflets.*—Number: Average 3 or 5. Size: About 65 mm. long and 40 mm. wide. Shape: Oval with denticulate margin. Texture: Leathery. Aspect: Smooth and glossy. Color: Upper side — Green 137-A. Under side — Yellow-green 144-B. Stipules: Adnate with little hairs. Petiolule: 1 mm. Petioles: Length: About 12 mm. Rachis: Smooth and with a sparse number of small spines.

Thorns:

*Size.*—About 1 mm. long.

*Color.*—Yellow-green 147-D.

THE BUD

Size: Large commercial sized bud.

*Diameter.*—About 34 mm.

*Length.*—About 36 mm.

Shape: High centered and pointed.

Opening rate: Slow.

Color of petals:

*When sepals first divide.*—155-D.

*When petals begin to unfurl.*—155-B.

Sepals:

*Number.*—Five.

*Shape.*—Lanceolate.

*Character.*—Hooded over the bud until ready to divide and when the flowers open, the sepals curl back.

*Color.*—Inside — Greyed green 191-B covered with white hairs. Outside — Yellow-green 144-C.

Calyx:

*Shape.*—Funnel-shaped.

*Size.*—Large and broad.

*Splitting.13* Calyx does not split.

*Aspect.*—Smooth.

Peduncle of flower stem:

*Length.*—About 108 mm.
*Aspect.*—Smooth with sparse hairs.
*Character.*—Rigid and erect.
*Color.*—Yellow-green 144-A.

THE FLOWER

Blooming habit: Continuous and profusely, from early Spring to Winter, blooming freely under greenhouse conditions.
Size of bloom: Large.
*Diameter.*—About 12 cm.
*Depth.*—About 40 mm.
Borne: Singly on strong, erect stems.
Shape:
*When bloom first opens.*—Cup shaped with high center.
*When bloom matures.*—A widened cup with high center and petals very nicely imbricated.
Petalage:
*Number.*—About 41.
*Arrangement.*—Imbricated.
*Form.*—Generally oval with ruffled margin and slightly pointed apex.
*Texture.*—Leathery and soft.
*Aspect.*—Velvety.
*Color.*—Outer petals body — White 155-B. Base — Green-yellow 1-D. Inside petals body — 155-D. Base — Yellow 2- D.
Petaloids:
*Number.*—About 13.
*Size.*—20 mm. long and 11 mm. wide.
*Color.*—White 155-D. Base — Green-yellow 1-D.
Peduncle:
*Length.*—About 108 mm.

*Color.*—Yellow-green 144-A.
*Character.*—Sturdy and upright, but slightly curving.
Fragrance: Slight.
Discoloration after full bloom: Slight.
Persistance: An average of 6 to 9 days as a cut flower.
Disease resistance: Moderately resistant to mildew, black spots and rust as observed at Pleasanton, Calif.

THE REPRODUCTIVE ORGANS

Stamens:
*Number.*—About 76.
*Arrangement.*—Slightly introse.
*Anthers.*—Size: About 3 mm. Color: Yellow-orange 22-B.
*Filaments.*—Length: About 8 mm. Color: Yellow-green 154-D.
*Pollen.*—Color: Yellow-orange 22-B.
Pistils:
*Number.*—About 156.
*Styles.*—Length: About 8 mm. Color: Yellow-green 154-D.
*Stigmas.*—Color: Yellow 8-C.
Character of the ovaries: Oval shaped, slightly flattened on one side and entirely covered with white hairs.

I claim:

1. The new and distinctive greenhouse rose substantially as herein shown and described, characterized in particular by its continuous and profuse production of large white flowers carried on strong upright stems of medium length, grown from a sturdy, upright, free branching plant with abundant foliage.

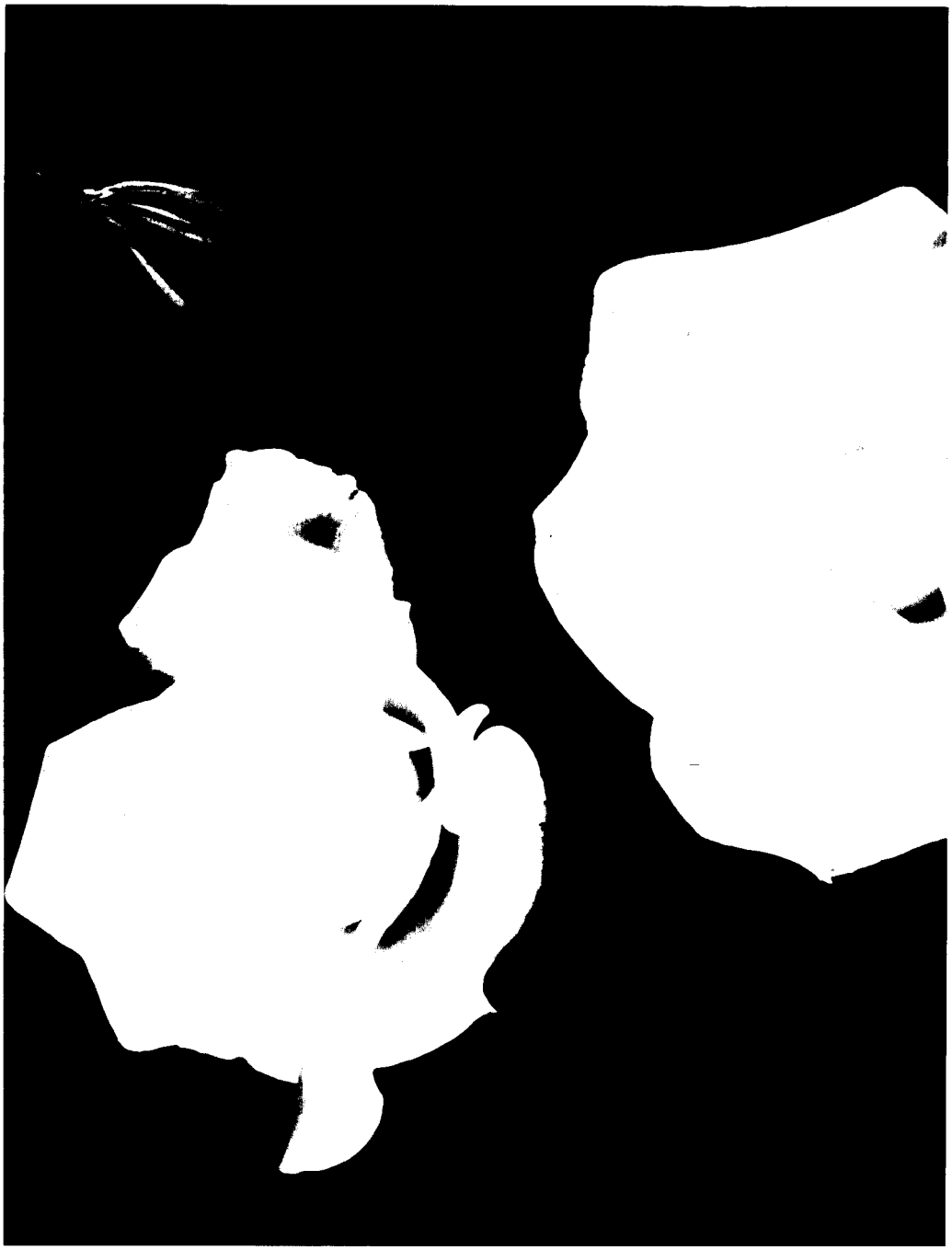

* * * * *